United States Patent [19]

Miller

[11] Patent Number: 5,250,694
[45] Date of Patent: Oct. 5, 1993

[54] PROCESS FOR THE PREPARATION OF 2,3-PYRIDINE-DICARBOXYLIC ACIDS FROM 3-(2-IMIDAZOLIN-2-YL)PICOLINIC ACIDS

[75] Inventor: Paul E. Miller, Palmyra, Mo.

[73] Assignee: American Cyanamid Company, Stamford, Conn.

[21] Appl. No.: 935,957

[22] Filed: Aug. 26, 1992

[51] Int. Cl.⁵ ............................................. C07D 401/04
[52] U.S. Cl. ................................. 546/321; 546/322; 546/168
[58] Field of Search .................. 546/321, 322, 168

[56] References Cited

U.S. PATENT DOCUMENTS

| | | | |
|---|---|---|---|
| 4,460,776 | 7/1984 | Wepplo | 546/250 |
| 4,658,030 | 4/1987 | Barton et al. | 546/167 |
| 4,798,619 | 1/1989 | Los | 511/66 |

OTHER PUBLICATIONS

Chemical Abstracts, vol. 109, No. 3, Abstract 22.968t, p. 620, Jul. 18, 1988.
Brewster, *Organic Chemistry*, 3rd Edition, p. 238, 1961.

*Primary Examiner*—C. Warren Ivy
*Assistant Examiner*—Zinna N. Davis
*Attorney, Agent, or Firm*—Peggy A. Climenson

[57] ABSTRACT

There is provided a process for the preparation of a 2,3-pyridinedicarboxylic acid from a 3-(2-imidazolin-2-yl)picolinic acid. The 2,3-pyridinedicarboxylic acids are useful in the preparation of herbicidal 2-(2-imidazolin-2-yl)nicotinic and quinoline-3-carboxylic acids, esters and salts.

13 Claims, No Drawings

PROCESS FOR THE PREPARATION OF 2,3-PYRIDINE-DICARBOXYLIC ACIDS FROM 3-(2-IMIDAZOLIN-2-YL)PICOLINIC ACIDS

BACKGROUND OF THE INVENTION 2,3-Pyridinedicarboxylic acids are useful in the preparation of herbicidal 2-(2-imidazolin-2-yl)nicotinic and quinoline-3-carboxylic acids, esters and salts. In the manufacture of these herbicidal compounds, aqueous media containing undesirable 3-(2-imidazolin-2-yl)picolinic acid by-products are obtained.

Heretofore, these 3-(2-imidazolin-2-yl)picolinic acid by-products served no utitity and were disposed of by incineration. Now it has been found that the undesirable 3-(2-imidazolin-2-yl)picolinic acid by-products can be recycled by conversion to 2,3-pyridinedicarboxylic acids, useful starting materials for the manufacture of herbicidal 2-(2-imidazolin-2-yl)nicotinic and quinoline-3-carboxylic acids, esters and salts, thus eliminating the need for disposal and resulting in significant environmental and cost benefits.

U.S. Pat. No. 4,658,030 describes the base-catalyzed cyclization of carbamoyl nicotinic acids and carbamoyl 3-quinolinecarboxylic acids to herbicidal 2-(2-imidazolin-2-yl)compounds. U.S. Pat. No. 4,658,030 also describes the ring opening conversion of 2-(2-imidazolin-2-yl)compounds to carbamoyl nicotinic acids and carbamoyl 3-quinolinecarboxylic acids in the presence of base. However, the patentees do not describe a method for the conversion of 3-(2-imidazolin-2-yl)picolinic acids to 2,3-pyridinedicarboxylic acids.

It is an object of the present invention to provide an efficient and effective process for the preparation of 2,3-pyridinedicarboxylic acids from undesirable 3-(2-imidazolin-2-yl)picolinic acids.

SUMMARY OF THE INVENTION

The present invention relates to a process for the preparation of 2,3-pyridinedicarboxylic acids of formula I

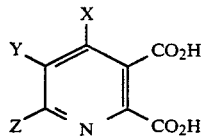

(I)

wherein

X is hydrogen or methyl; and
Y and Z are each independently hydrogen, halogen, $C_1-C_6$ alkoxy, $C_1-C_4$ alkylthio, $C_1-C_6$ alkyl optionally substituted with one to three $C_1-C_4$ alkoxy groups, phenoxy optionally substituted with one $C_1-C_4$ alkyl or $C_1-C_4$ alkoxy group, or phenyl optionally substituted with one $C_1-C_4$ alkyl or $C_1-C_4$ alkoxy group; and, when taken together, Y and Z may form a ring in which YZ is represented by the structure: —$(CH_2)_n$—, where n is an integer of 3 or 4, or

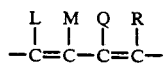

where L, M, Q and R are each independently hydrogen, $C_1-C_4$ alkyl or $C_1-C_4$ alkoxy.

Surprisingly, it has been found that 2,3-pyridinedicarboxylic acids of formula I may be prepared efficiently and effectively in a two step process by reacting an undesirable, by-product 3-(2-imidazolin-2-yl)picolinic acid of formula II

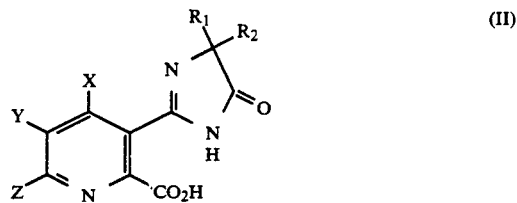

(II)

wherein X, Y and Z are as described above, $R_1$ is $C_1-C_4$ alkyl and $R_2$ is $C_1-C_4$ alkyl or $C_3-C_6$ cycloalkyl, and when $R_1$ and $R_2$ are taken together with the carbon atom to which they are attached they may represent $C_3-C_6$ cycloalkyl optionally substituted with methyl, with a metal hydroxide in the presence of water to form a 3-[(1-carbamoylpropyl)carbamoyl]picolinic acid of formula III

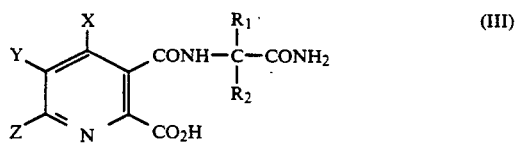

(III)

wherein X, Y, Z, $R_1$ and $R_2$ are as described above and reacting said formula III compound with an acid in the presence of water to form the desired 2,3-pyridinedicarboxylic acid of formula I.

Advantageously, the present invention provides an efficient and effective process for converting undesirable 3-(2-imidazolin-2-yl)picolinic acids to desirable 2,3-pyridinedicarboxylic acids which are used in the manufacture of herbicidal 2-(2-imidazolin-2-yl)nicotinic and quinoline-3-carboxylic acids, esters and salts. By converting the 3-(2-imidazolin-2-yl)picolinic acids to useful starting materials, the overall product yields of the herbicidal compounds are improved through conversion of undesirable by-products into starting materials.

DETAILED DESCRIPTION OF THE INVENTION

The present invention provides an efficient and effective two step process for converting an undesirable formula II 3-(2-imidazolin-2-yl)picolinic acid to a desirable formula I 2,3-pyridinedicarboxylic acid. The 2,3-pyridinedicarboxylic acid may be integrated into an existing preparative process for a herbicidal 2-(2-imidazolin-2-yl)nicotinic or quinoline-3-carboxylic acid, ester or salt.

Formula I 2,3-pyridinedicarboxylic acids are efficiently and effectively prepared by reacting a formula II 3-(2-imidazolin-2-yl)picolinic acid with a metal hydroxide in the presence of water to form a formula III 3-[(1-carbamoylpropyl)carbamoyl]picolinic acid and reacting said formula III compound with an acid in the presence of water to form the desired formula I 2,3-pyridinedicarboxylic acid. The above reaction scheme is shown in Flow Diagram I.

FLOW DIAGRAM I

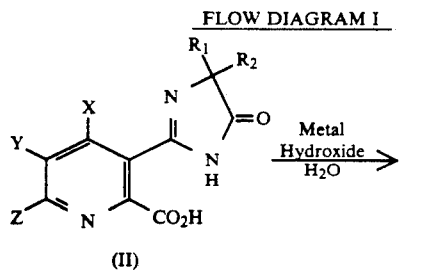

(II)

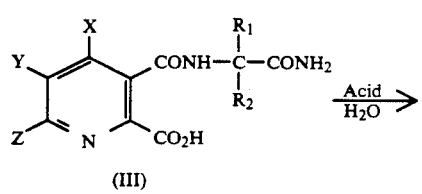

(III)

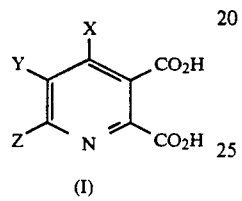

(I)

The process of the present invention preferably comprises reacting a formula II 3-(2-imidazolin-2-yl)picolinic acid with a metal hydroxide in the presence of water at a pH range of from about pH 8.5 to pH 11.5, preferably from about pH 9.0 to pH 11.0, and at a temperature range of from about 20° C. to 120° C. to form a formula III 3-[(1-carbamoylpropyl)carbamoyl]picolinic acid. Said formula III compound is then reacted with an acid in the presence of water at a pH range of from about pH 1.0 to pH 4.0, preferably from about pH 1.5 to pH 3.5, and at a temperature range of from about 20° C. to 120° C. to form the desired formula I 2,3-pyridinedicarboxylic acid.

The process of the present invention is especially useful for the preparation of formula I compounds wherein X is hydrogen; and Y and Z are each independently hydrogen or $C_1$–$C_6$ alkyl optionally substituted with one to three $C_1$–$C_4$ alkoxy groups; and, when taken together, Y and Z may form a ring in which YZ is represented by the structure:

—CH=CH—CH=CH—.

Preferred formula I compounds prepared according to the process of the present invention are 5-ethyl-2,3-pyridinedicarboxylic acid, 2,3-pyridinedicarboxylic acid, 5-methyl-2,3-pyridinedicarboxylic acid, 5-(methoxymethyl)-2,3-pyridinedicarboxylic acid and 2,3-quinolinedicarboxylic acid.

The product formula I compounds may be isolated by filtration of the formula I product or by extraction of the reaction mixture with a suitable solvent. In the isolation procedure suitable extraction solvents include tetrahydrofuran and water-immiscible alcohols.

Advantageously, the product formula I compounds may also be isolated by extracting the reaction mixture with a binary solvent system. The process for extracting pyridine- and quinolinedicarboxylic acids from aqueous media utilizing a binary solvent system is described in copending U.S. patent application Ser. No. 07/829,397 filed on Feb. 4, 1992.

Metal hydroxides suitable for use in the process of the present invention include alkali metal hydroxides and alkaline earth metal hydroxides. Preferred alkali metal hydroxides are sodium hydroxide and potassium hydroxide.

Acids suitable for use in the above process of the invention include mineral acids, trifluoroacetic acid, trichloroacetic acid, dichloroacetic acid and the like. Preferred mineral acids are sulfuric acid, hydrochloric acid and hydrobromic acid.

Formula I 2,3-pyridinedicarboxylic acids are useful in the preparation of highly effective herbicidal 2-(2-imidazolin-2-yl)nicotinic and quinoline-3-carboxylic acids, esters and salts of formula IV

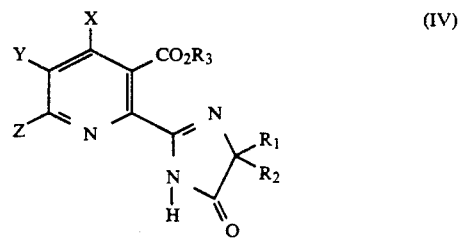

wherein $R_3$ is hydrogen, an ester or a cation; and X, Y, Z, $R_1$ and $R_2$ are as described above for formula II.

Among the methods of preparation for a formula IV herbicidal compound which utilizes the corresponding formula I 2,3-pyridinedicarboxylic acid are those described in U.S. Pat. Nos. 4,460,776 and 4,798,619.

In order to facilitate a further understanding of the invention, the following examples are presented to illustrate more specific details thereof. The invention is not to be limited thereby except as defined in the claims. All weight/weight percents are determined by high performance liquid chromatography analyses.

EXAMPLE 1

Preparation of 5-Ethyl-2,3-pyridinedicarboxylic acid from an aqueous medium containing 5-ethyl-3-(4-isopropyl-4-methyl-5-oxo-2-imidazolin-2-yl)picolinic acid

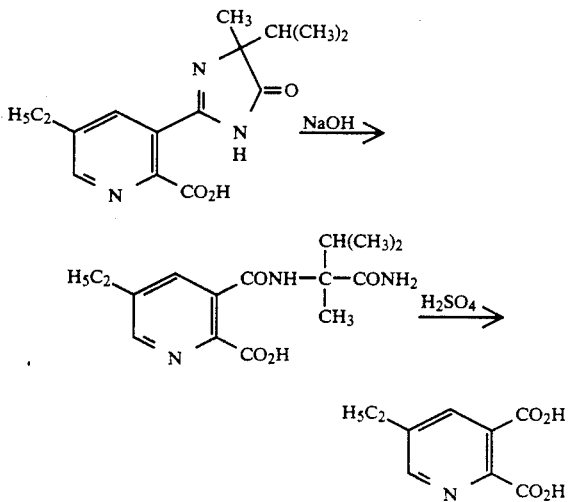

An aqueous medium (300 g) containing 0.51 wt/wt % 5-ethyl-2,3-pyridinedicarboxylic acid, 16.05 wt/wt % 5-ethyl-3-(4-isopropyl-4-methyl-5-oxo-2-imidazolin-2-yl)picolinic acid, 0.90 wt/wt % 3-[(1-carbamoyl-1,2-dimethylpropyl)carbamoyl]-5-ethylpicolinic acid and 5.37 wt/wt % other by-products is adjusted to pH 9.9 with 50% sodium hydroxide solution (11.2 g, 0.23 mol) and sulfuric acid (3.1 g, 0.03 mol). The reaction mixture is heated at reflux for 90 hours and found to contain 0.67 wt/wt % 5-ethyl-2,3-pyridinedicarboxylic acid, 3.8 wt/wt % 5-ethyl-3-(4-isopropyl-4-methyl-5-oxo-2-imidazolin-2-yl)picolinic acid, 14.56 wt/wt % 3-[(1-carbamoyl-1,2-dimethylpropyl)carbamoyl]-5-ethyl-picolinic acid and 5.51 wt/wt % other by-products. The reaction mixture is then adjusted to pH 2.0 with sulfuric acid (50 g, 0.51 mol), heated at reflux for 7 hours and found to contain 5.55 wt/wt % 5-ethyl-2,3-pyridinedicarboxylic acid, 0.0% wt/wt % 5-ethyl-3-(4-isopropyl-4-methyl-5-oxo-2-imidazolin-2-yl)picolinic acid, 2.65 wt/wt % 3-[(1-carbamoyl-1,2-dimethylpropyl)carbamoyl]-5-ethylpicolinic acid and 6.79 wt/wt % other by-products.

This example shows that by converting undesirable, by-product 5-ethyl-3-(4-isopropyl-4-methyl-5-oxo-2-imidazolin-2-yl)picolinic acid to useful 5-ethyl-2,3-pyridinedicarboxylic acid, the amount of 5-ethyl-2,3-pyridinedicarboxylic acid present in the aqueous medium is increased by over a thousand percent.

EXAMPLE 2

Preparation of 2,3-Pyridinedicarboxylic acid compounds

Following essentially the same procedure described in Example 1 and substituting the appropriate aqueous media, the following compounds are prepared: 2,3-pyridinedicarboxylic acid, 5-methyl-2,3-pyridinedicarboxylic acid, 5-(methoxymethyl)-2,3-pyridinedicarboxylic acid, and 2,3-quinolinedicarboxylic acid.

EXAMPLE 3

Preparation of 5-Ethyl-2,3-pyridinedicarboxylic acid

A solution of 5-ethyl-3-(4-isopropyl-4-methyl-5-oxo-2-imidazolin-2-yl)picolinic acid (25.0 g, 92% real, 79.5 mmol) in water (150 g) is adjusted to pH 10.2 with sodium hydroxide, heated at reflux for 6 hours, stirred overnight at room temperature, adjusted to pH 9.7 with sulfuric acid, heated at reflux for 3 hours and found to contain 0.05 wt/wt % 5-ethyl-2,3-pyridinedicarboxylic acid, 12.48 wt/wt % 3-[(1-carbamoyl-1,2-dimethylpropyl)carbamoyl]-5-ethylpicolinic acid and 2.72 wt/wt % 5-ethyl-3-(4-isopropyl-4-methyl-5-oxo-2-imidazolin-2-yl)picolinic acid. The reaction mixture is then adjusted to pH 2.2 with sulfuric acid, heated at reflux for 8 hours and found to contain 3.29 wt/wt % 5-ethyl-2,3-pyridinedicarboxylic acid, 0.69 wt/wt % 3-[(1-carbamoyl-1,2-dimethylpropyl)carbamoyl]-5-ethylpicolinic acid and 0.0 wt/wt % 5-ethyl-3-(4-isopropyl-4-methyl-5-oxo-2-imidazolin-2-yl)picolinic acid.

I claim:

1. A process for the preparation of a 2,3-pyridinedicarboxylic acid of formula I

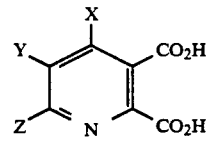

wherein
X is hydrogen or methyl; and
Y and Z are each independently hydrogen, halogen, $C_1$-$C_6$ alkoxy, $C_1$-$C_4$ alkylthio, $C_1$-$C_6$ alkyl optionally substituted with one to three $C_1$-$C_4$ alkoxy groups, phenoxy optionally substituted with one $C_1$-$C_4$ alkyl or $C_1$-$C_4$ alkoxy group, or phenyl optionally substituted with one $C_1$-$C_4$ alkyl or $C_1$-$C_4$ alkoxy group; and,
when taken together, Y and Z may form a ring in which YZ is represented by the structure: —($CH_2$)$_n$—, where n is an integer of 3 or 4, or

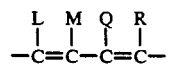

where L, M, Q and R are each independently hydrogen, $C_1$-$C_4$ alkyl or $C_1$-$C_4$ alkoxy, which comprises reacting a 3-(2-imidazolin-2-yl)picolinic acid of formula II

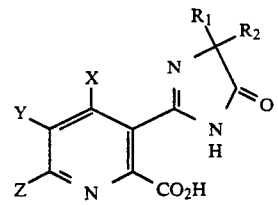

wherein X, Y and Z are as described above, $R_1$ is $C_1$-$C_4$ alkyl and $R_2$ is $C_1$-$C_4$ alkyl or $C_3$-$C_6$ cycloalkyl, and when $R_1$ and $R_2$ are taken together with the carbon atom to which they are attached they may represent $C_3$-$C_6$ cycloalkyl optionally substituted with methyl, with a metal hydroxide in the presence of water at a pH range from about pH 8.5 to pH 11.5 and at a temperature range from about 20° C. to 120° C. to form a 3-[(1-carbamoylpropyl)carbamoyl]picolinic acid of formula III

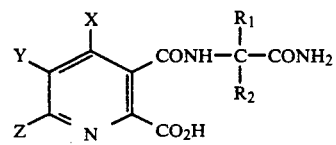

wherein X, Y, Z, $R_1$ and $R_2$ are as described above and reacting said formula III compound with an acid in the presence of water at a pH range from about pH 1.0 to pH 4.0 and at a temperature range from about 20° C. to 120° C. to form the desired formula I 2,3-pyridinedicarboxylic acid.

2. The process according to claim 1 wherein the metal hydroxide is selected from the group consisting of an alkali metal hydroxide and an alkaline earth metal hydroxide.

3. The process according to claim 2 wherein the alkali metal hydroxide is selected from the group consisting of sodium hydroxide and potassium hydroxide.

4. The process according to claim 1 wherein the acid is a mineral acid.

5. The process according to claim 4 wherein the mineral acid is selected from the group consisting of sulfuric acid, hydrochloric acid and hydrobromic acid.

6. The process according to claim 1 wherein the pH is from about pH 9.0 to pH 11.0.

7. The process according to claim 1 wherein the pH is from about pH 1.5 to pH 3.5.

8. The process according to claim 1 wherein

X is hydrogen;

Y and Z are each independently hydrogen or $C_1$–$C_6$ alkyl optionally substituted with one to three $C_1$–$C_4$ alkoxy groups; and, when taken together, Y and Z may form a ring in which YZ is represented by the structure:

—CH=CH—CH=CH—; and $R_1$ and $R_2$ are each independently $C_1$–$C_4$ alkyl.

9. The process according to claim 8 wherein the formula I compound is 5-ethyl-2,3-pyridinedicarboxylic acid.

10. The process according to claim 8 wherein the formula I compound is 2,3-pyridinedicarboxylic acid.

11. The process according to claim 8 wherein the formula I compound is 5-methyl-2,3-pyridinedicarboxylic acid.

12. The process according to claim 8 wherein the formula I compound is 5-(methoxymethyl)-2,3-pyridinedicarboxylic acid.

13. The process according to claim 8 wherein the formula I compound is 2,3-quinolinedicarboxylic acid.

* * * * *